United States Patent [19]

Judge

[11] 4,067,242
[45] Jan. 10, 1978

[54] MOLTEN METAL SAMPLING DEVICE AND METHOD

[75] Inventor: James R. Judge, Weirton, W. Va.

[73] Assignee: National Steel Corporation, Pittsburgh, Pa.

[21] Appl. No.: 653,911

[22] Filed: Jan. 30, 1976

Related U.S. Application Data

[63] Continuation-in-part of Ser. No. 525,230, Nov. 19, 1974, abandoned.

[51] Int. Cl.² .............................................. G01N 1/14
[52] U.S. Cl. ................................. 73/425.6; 73/DIG. 9
[58] Field of Search .......... 73/425.6, 425.4 R, DIG. 9

[56] References Cited

U.S. PATENT DOCUMENTS 3,686,949  8/1972  Hackett ...................... 73/DIG. 9 X
3,704,621 12/1972  Zickefoose et al. ............ 73/425.4 R

OTHER PUBLICATIONS

Chemical Abstracts, vol. 67, No. 6, 1967 (24239u & 24240n).
A Metallurgical Study of the Production of Fe–Ni Alloys. Iehinose, "Nippon Kinzoku Gakkaishi" 29(3), pp. 287–301 (1965) (Japan).

*Primary Examiner*—Richard C. Queisser
*Assistant Examiner*—Joseph W. Roskos
*Attorney, Agent, or Firm*—Shanley, O'Neil & Baker

[57] ABSTRACT

Molten metal sampling device for and method of sampling molten unkilled metal, especially steel, to produce a sound, non-porous, solidified test sample suitable for analysis in which metallic germanium is present in the sampling device in a quantity sufficient to kill the molten metal of the sample.

9 Claims, 8 Drawing Figures

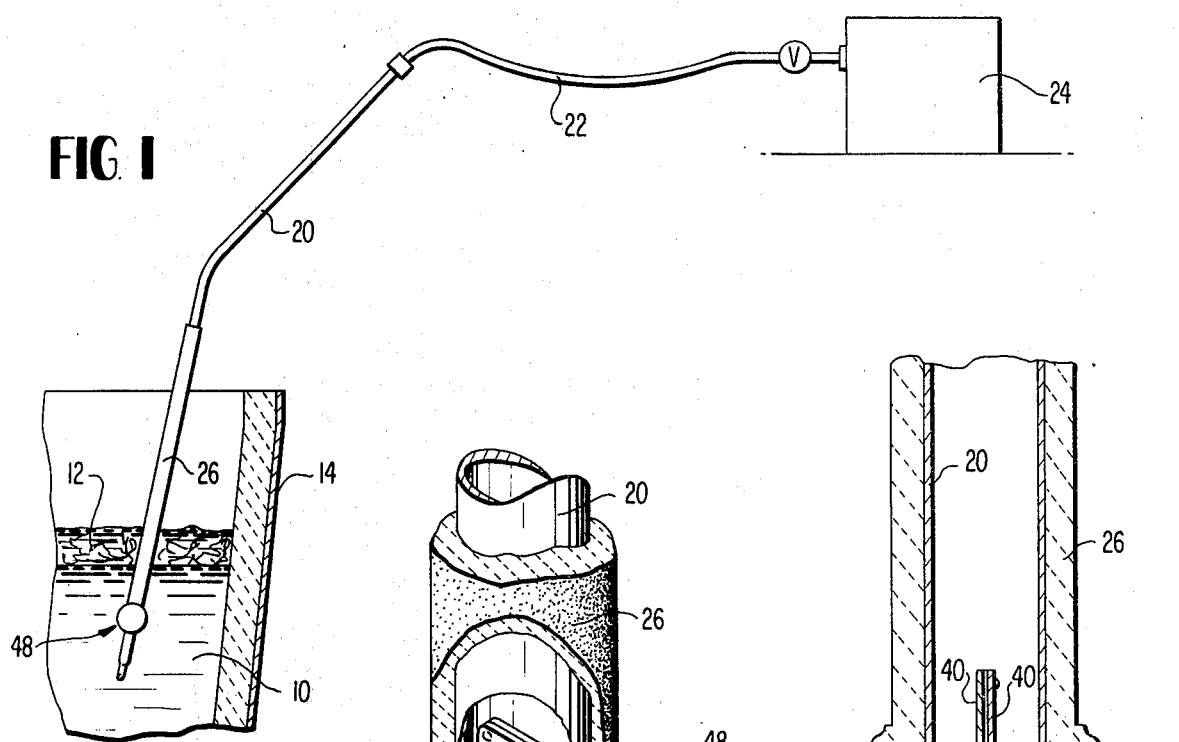
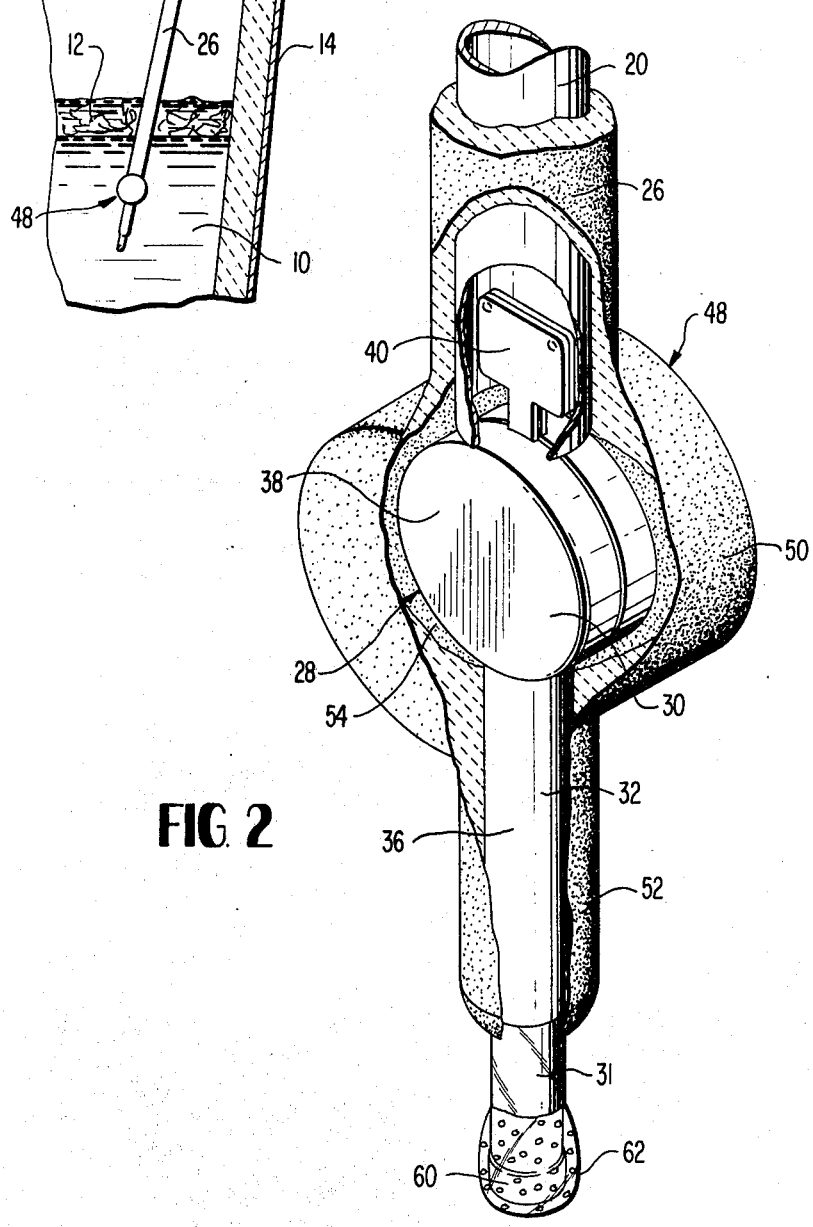
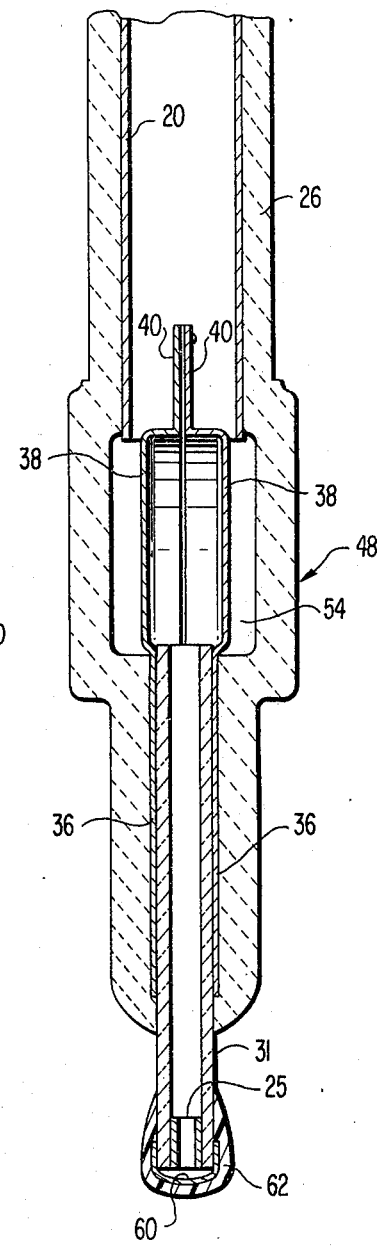
FIG. 1
FIG. 2
FIG. 3

TITANIUM KILLED-AVERAGE IN NORMAL SAMPLING ARE

MOLTEN METAL SAMPLING DEVICE AND METHOD

CROSS-REFERENCE TO RELATED APPLICATION

This is a continuation-in-part of application Ser. No. 525,230, filed Nov. 19, 1974 now abandoned.

BACKGROUND OF THE INVENTION

It has been the practice when sampling molten unkilled steel to use in the sampling device a killing agent such as aluminum, zirconium, silicon or titanium. The unkilled steel is introduced into a cavity in the sampling device where the killing agent is present in sufficient quantity to combine with the available oxygen of the molten sample so that upon freezing of the sample there will be no substantial loss of oxygen content and no porosity which will interfere with analysis. When used in this sense, the terms "killed" and "killing" do not have the same meaning that they would have in refining operations where such terms indicate deoxidation of the molten steel to such an extent that it will lie quiescent when poured into an ingot mold. Obviously, such a deoxidation procedure would not be used if one intended to analyze the oxygen content of a sample of the molten steel since it would be self-defeating. Therefore, when used in the present disclosure, the terms "killed" or "killing" should be construed as the chemical combination of a metal with available, i.e., free, oxygen in a sample.

The use of previously known killing agents in sampling has many attendant problems. For example, when aluminum or silicon are used, two samples must be taken since the analysis of steel usually seeks silicon and aluminum content. The same is often true in the case of zirconium and titanium. Zirconium has the additional disadvantage of making the solidified sample hard and therefore more difficult to work with. Titanium also has an additional disadvantage in that it makes the sample tough and more difficult to work with. Perhaps most disadvantageous, titanium is difficult to melt in sampling devices and unmelted concentrations of titanium throw the analysis results off. Even when it does melt, titanium, and other previously known killing agents, will react with at least a portion of the available nitrogen in the sample to form higher melting nitrides and thus promote inaccurate nitrogen readings.

U.S. Pat. No. 3,704,621 proposes the use of magnesium in lieu of the above killing agents in sampling molten unkilled steel and it does an excellent job. However, its use is limited, and special care is required to avoid the propinquity of the magnesium to combine with air at molten steel temperatures and create explosive conditions.

As a result of all the foregoing, the steel industry has lacked a satisfactory killing agent for use in the sampling of molten steel.

SUMMARY OF THE INVENTION

Applicant has made the discovery that germanium is the answer to the steel industry's problem in killing molten samples for the following reasons.

Germanium is not an element which is looked for in analysis in steel and eliminates the need for taking extra samples such as where aluminum, silicon, zirconium and titanium are used. Germanium melts at about two-thirds the melting point of iron and boils at about the same temperature as iron; consequently germanium would melt rapidly and remain molten for maximum diffusion through the molten metal better than the killing elements now in, other than aluminum. By the same token, germanium would not prematurely boil out or solidify. Germanium has a density much closer to iron than any of the other elements used in testing and this should result in less problems of loss by flotation. The natural valence of the element results in less quantity of weight required to kill the steel. Germanium has a thermal conductivity nearly identical to that of iron. The addition of germanium to a molten sample will not toughen the steel, even though it may harden the steel slightly like silicon, thereby eliminating many punching and cutting problems associated with titanium. Germanium is not poisonous, dangerous and explosive to handle. Germanium is available on the market at a reasonable price if purchased in quantity; it can be formed and cut to special shapes and may be alloyed with other elements.

Applicant has discovered that oxides formed by germanium readily react with hot graphite to eliminate combustion problems in oxygen determinators, which discovery is the subject matter of applicant's copending patent application Ser. No. 701,029, filed June 29, 1976.

BRIEF DESCRIPTION OF THE DRAWINGS

In the accompanying drawings which illustrate specific embodiments of applicant's invention:

FIG. 1 is a view of an embodiment in the environment of use;

FIG. 2 is a perspective view of the embodiment of FIG. 1 with parts broken away for better illustration;

FIG. 3 is a view in cross section taken on the line 3—3 of FIG. 2;

DESCRIPTION OF THE PREFERRED EMBODIMENTS

Figure 4:
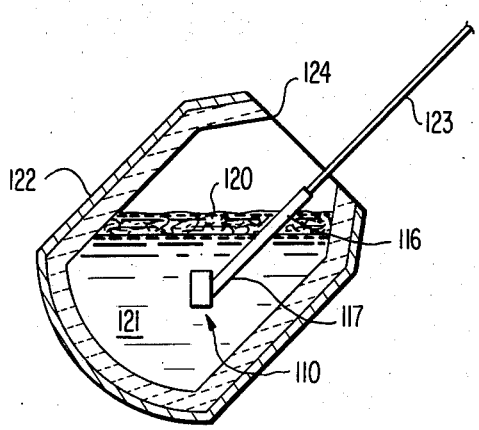
FIG. 4 is a view of another embodiment in the environment of use.

This invention may be utilized in the analysis of molten metal in general. However, when utilizing the pin and disc sampler described hereinafter the invention is particularly useful in the analysis of metals having a melting point up to about 3200° F (1760° C), including, for example, STELLITE (alloys containing 40 to 80% cobalt, 20 to 35% chromium, 0 to 25% tungsten, 0.75 to 2.5% carbon, and 0 to 3% silicon), as well as lead, copper, titanium, tungsten, molybdenum, columbium and thorium based alloys. In a preferred embodiment, as indicated in the ensuing discussion, the method and apparatus of this invention are utilized in the analysis of steel.

Referring to the drawing and especially FIG. 1, a bath or pool of molten steel 10 having on its surface a layer of slag or casting powder 12 is held within a refractory lined receptacle, treating vessel or tundish 14. Where the receptable is a continuous casting mold the refractory of course is not present. A sampling device indicated generally at 18 is shown projecting through the layer of slag 12 into the bath of molten metal 14. The sampling device is carried on the lower end of a long, rigid conduit or pipe 20 which has attached to its upper end by means of a flexible hose 22 an evacuating device 24 such as a mechanical roughing vacuum pump. The portion of pipe 20 projecting into the bath is protected by a refractory sheath 26.

Referring to FIG. 2, the sampling mold component of sampling device 18 is indicated generally at 28. This mold is made up of a hollow, flat metallic section indicated at 30 for forming the desired disc sample, a fused quartz tube 31 for forming the desired pin sample and a cylindrical metallic holder 32 for the quartz tube carried by section 30. Where desired the sample mold need not include provision for forming a disc sample. The metallic portion of mold 28 is made up of two identical halves each half being made up of a semi-cylindrical portion 36, a pan shape portion 38 and projecting ear means 40 for holding the component halves together but sufficiently spaced so as to place the interior of the disc shaped mold in gaseous communication with the space surrounding the disc shaped mold. Ear means 40 are formed from a couple of slightly tapered ears which are spot welded together, the resulting structure being wedgeable into the lower end of pipe 20 to hold sample mold 28 rigidly in place at the lower end of pipe 20.

The two pan shaped elements 38 form the disc sample mold section and the semi-cylindrical elements 36 carried by pan shaped elements 38 embrace and hold fused quartz tube 31 which is at least as long as a desired pin sample. The open upper end of quartz tube 31 opens into the interior of disc sample mold 30 and therefore the interior of quartz tube 31 is in open communication with the interior of disc sample mold 30.

Preferably integrally molded on the lower end of refractory sheath 26 is an impervious refractory casing indicated generally at 48 formed of a section 50 surrounding and in spaced relation to disc sample mold 30 and an integral depending tubular portion 52 preferably molded around the cylindrical metallic holder section 36 with the lower portion of tubular portion 52 molded around and holding quartz tube 31 in place while leaving the lowermost portion of quartz tube 31 exposed. Since casing 48 is integrally molded onto sheath 26 and tubular extension 52 is integrally molded onto enlarged portion 50 of casing 48 and since tubular extension 52 of the refractory casing is molded onto and in sealing relation with quartz tube 31, the interior of refractory casing 48 can be subjected to the vacuum generated at means 24 between mold section 30 and section 50 of the refractory casing. Space 54 acts as thermal insulator and conduit for applying vacuum to mold 30 interior. This last is because the pan shaped halves of mold 30 are slightly spaced and not in sealing contact with each other and when subatmospheric gas pressure is present in the cavity 54 it is present within the disc sample mold 30 and the interior of fused quartz tube 44.

In order to preserve the interior of the sample molds free from contamination prior to taking a sample, the lower open end of quartz tube 31 is closed by a metal cap 60, which in turn is enveloped by a plastic coating 62 entirely covering the cap and extending beyond the cap around and in continuous sealing contact with the exterior surface of fused quartz tube 31 in the neighborhood of the cap 60 so as to seal cap 60 to the lower end of quartz tube 31 and thereby maintain the interior of the entire system under subatmospheric pressure generated at means 24. Metal cap 60 is preferably formed of a metal, such as mild steel, which has no constituents which would interfere with test results.

The coating 62 is a continuous, homogeneous plastic coating. The composition of this plastic and the thickness of the plastic coating enter into the present invention in addition to the sealing function of the plastic. The composition of this plastic material and the thickness of the plastic coating is such that introduction and movement of the sampling device into and through the surface layer of slag or fluxing material on the molten metal and thence into the body of molten metal to be sampled will result in the plastic material decomposing into gaseous form at a rate and in a quantity to remove completely from proximity to the exterior walls of the lower end portion of the fused quartz tube any slag or fluxing material which otherwise would be adhering to the lower end portion of the fused quartz tube so as to contaminate the sample entering the mold.

The pin and disc sampling device of FIGS. 1 to 3 as so far described does not constitute part of the present invention, this sampling device being covered by co-pending patent application Ser. No. 514,177, filed Oct. 11, 1974 in the name of James R. Judge and Van L. Vierbicky, now Pat. No. 3,915,014.

Shown in the lower end of fused quartz tube 31 are solid buttons 25 of metallic germanium. The germanium may be present in different forms, the illustrated buttons being a convenient form although powdered germanium metal, germanium metal shavings, germanium metal wire could be used. Upon entry of the molten steel to be sampled into the lower end of fused quartz tube 31, the suction supplied by means 24 will draw the molten metal into contact with the metallic germanium buttons which are melted by the heat of the molten steel and mix or alloy with the molten steel which then passes up through the fused quartz tube and into disc sample mold 30. The germanium kills the molten steel sample by reacting with the available oxygen in the steel and forming germanium dioxide ($GeO_2$), or germanic oxide as it is sometimes called. Since germanic oxide (m.p. 1389° ± 4° K) is stable at the temperature of the molten steel it will remain in the sample. Upon cooling, the sample is then prepared for analytic procedures. Previously, it had been impossible to obtain a satisfactory killing of pin and disc samples because conventional killing agents which may be acceptable in other respects, such as titanium, will not melt and mix entirely in this type of sampler. However, germanium, because of its low melting point and density, will melt and mix thoroughly with the molten steel, at least in the cavity of mold section 30, and it will not float on the surface of the steel as the steel rises up into the cavities of mold 28.

Figure 6:
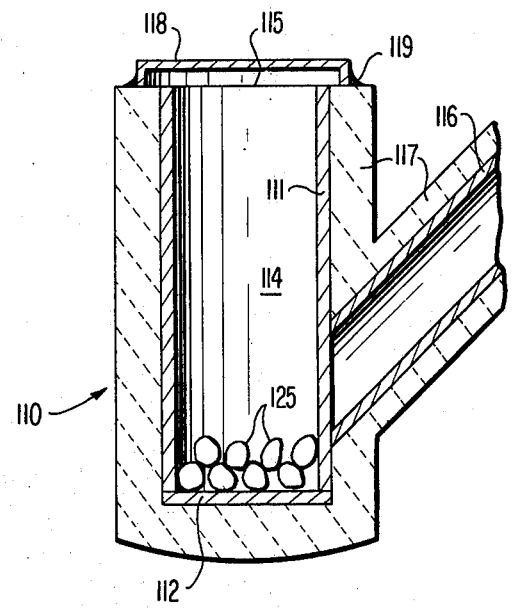
FIG. 6 is a vertical cross-sectional view of the sampling device of FIG. 5.
Figure 5:
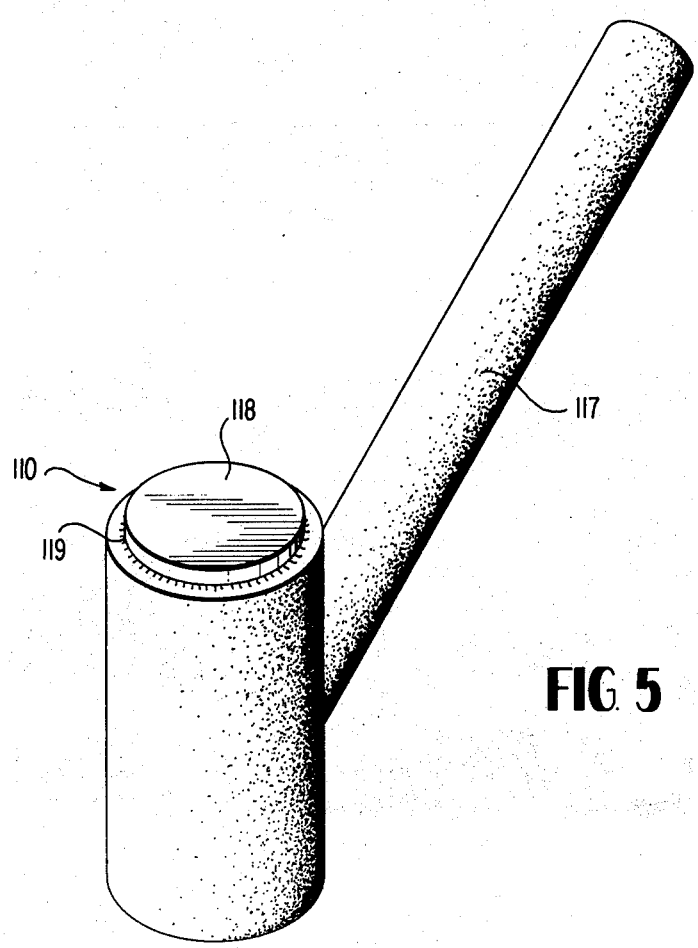
FIG. 5 is a perspective view of the embodiment of FIG. 4.

FIGS. 4 to 6 show a different type sampling device, namely, a "bomb" of the kind disclosed in U.S. Pat. No. 3,704,621.

As illustrated in FIG. 4, the molten steel sample enters the cavity of this type of sampler by hydrostatic pressure. In this embodiment, the sampling device, intended generally by reference numeral 110, includes an upright steel tubular member 111 which is open at its upper end and is closed off at its lower end by steel chill plate 112. The tubular member 111 and chill plate 112 define a cavity 114 for receiving the sample of molten steel, which is introduced through the opening 115. A steel tubular handle 16 is attached at its inner end to tubular member 111, and extends outward at a suitable angle to maintain the member 111 in an upright position when the sampling bomb 110 is immersed in a heat of steel to be sampled. The outer surfaces of tubular member 111, chill plate 112 and tubular handle 116 are coated with a layer of refractory material 117 such as fire clay. The opening 115 is sealed off by closure 118 which is adhesively attached along its marginal edge 119 to the refractory material 117. The closure 118 is constructed of a material which melts, decomposes or otherwise disintegrates when the sampling bomb 110 is immersed in a heat of molten unkilled steel, allowing a sample of molten unkilled steel to be introduced into cavity 114. Example of suitable materials for use in constructing closure 118 include metallic materials such as sheet steel, which do not contaminate the sample, and heat resistant paper which is preferably multilayered and sufficiently thick to withstand the temperature of the heat of steel for a period of time sufficient to allow the sampling bomb 110 to be immersed to the position illustrated in FIG. 4 of the drawings.

As is best seen in FIG. 4, the steel handle 116 and the refractory layer 117 thereon are sufficiently long to remain above the slag layer 120 when the sampling bomb 110 is immersed to a depth suitable for taking a sample of the heat of unkilled steel 121. A rod-like steel handle 123 is inserted into the outer end of tubular handle 116, and extends outward through opening 124 a distance suitable for allowing the sampling bomb 110 to be immersed within the heat of unkilled steel 121 by a workman.

This sampling device 110 incorporates solid buttons of metallic germanium 125 in the cavity 114. The germanium may be present in different forms, the illustrated buttons being a convenient form although powdered germanium metal, germanium metal shavings, germanium metal wire could be used.

The metallic germanium illustrated within the cavities of the two sampling devices shown in the drawings and described above is in an amount sufficient to kill the sample of molten unkilled steel flowing into each cavity. As a general rule, the molten unkilled steel sample introduced into the cavity of tube 31 and mold section 30 or into cavity 14 should be contacted with between about 0.01 to 1.0 percent by weight of metallic germanium, and preferably with between about 0.05 and 0.5 percent by weight. Usually the present invention is most effective at oxygen levels of 20 ppm to 500 ppm but higher oxygen levels may be present up to 2000 ppm. The amount of metallic germanium to be used in a given instance to achieve the best results will depend upon the oxygen level in the steel sample. For the best results, at least about 0.01 percent by weight of metallic germanium should be used for each 15 parts per million of oxygen in the unkilled steel sample. For example, when the unkilled steel sample is known to contain about 150 parts per million of oxygen, then at least about 0.1 percent by weight of metallic germanium should be contacted therewith; in the case of the FIGS. 4–6 sampling device, the sample weighs about 600 gms and the germanium metal button or buttons should thus weigh about 0.6 grams. At higher oxygen levels of 300, 450, 600, 750 and 1500 parts per million, the molten unkilled steel sample should be contacted with at least about 0.2%, 0.3%, 0.4%, 0.5% and 1.0% by weight of metallic germanium, respectively, to achieve the best results. It is understood that the molten steel sample is contacted with sufficient metallic germanium to produce a solidified test ingot which is killed. Except for the cost of the germanium metal, which is not excessive when purchased in quantity, the use of excess germanium metal is not objectionable since the germanium does not contaminate the sample with an element of analytical interest nor analytical detriment. When the metallic germanium is present in the quantities set out above, a properly killed test ingot can be produced which is solid and homogeneous and upon metallurgically polishing has no pin holes, inclusions and other imperfections.

Figure 7:
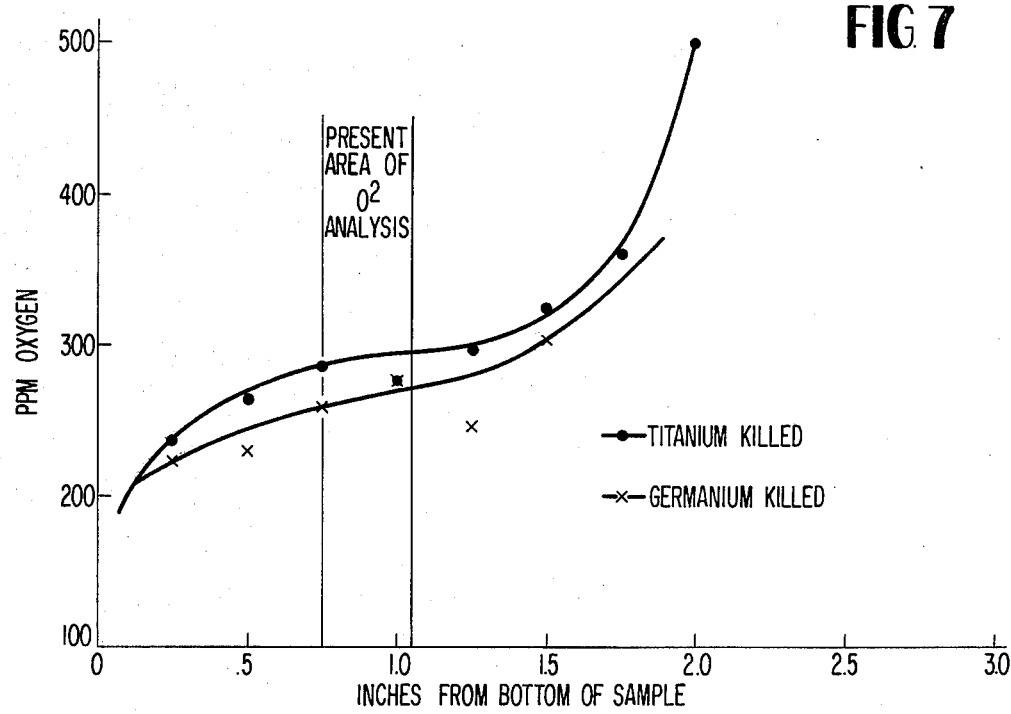
FIG. 7 and 8 are graphs illustrating the method of the invention.

Referring now to FIG. 7, two sampling devices of the type shown in FIGS. 4 to 6 carried in side-by-side relation by the same sampling lance were inserted into a ladle of steel from a basic oxygen furnace approximately two minutes after the regular post-tapping sample was taken. The two side-by-side sampling devices were loaded, one with the usual 1.88 grams of one thirty-second inch titanium wire, which is the usual titanium killing agent used, and the other with a 1 gram metal button of germanium. The post tapping samples taken right after tapping of the furnace showed that the oxygen content of the steel was 222 parts per million. Each sample was sectioned in small increments along the effective length of the sample in order to define clearly the shape of the oxygen distribution curve along the effective length of the sample. FIG. 7 shows the results. Both curves are of the usual shape with the oxygen content being indicated as low below the normal zone of analysis and the oxygen content increasing rapidly above the normal zone of oxygen analysis. This varying oxygen content is due to the difference in cooling rate between the lowermost part of the sample and the higher portions of the sample with a substantially true picture of the oxygen content appearing in the section of the sample starting at three-fourths of an inch from the bottom and extending to slightly above an inch above the bottom. From there on up the oxides lighter in weight than steel rising in the slower freezing metal and the occlusions being forced upwardly by the advancing face of the freezing metal result in a higher overall oxygen content which is not a true picture of the oxygen content of the molten steel taken into the sampling device. In other words, the metal in the zone of oxygen analysis has gained oxygen content from the metal below the zone and lost oxygen content to the metal above the zone with experience indicating that the zone of oxygen analysis chosen is representative of the oxygen content of the molten steel entering the sampling device. The curves of the graph of FIG. 7 show that metallic germanium indicates the oxygen distribution in the sample just as well as titanium does.

Figure 8:
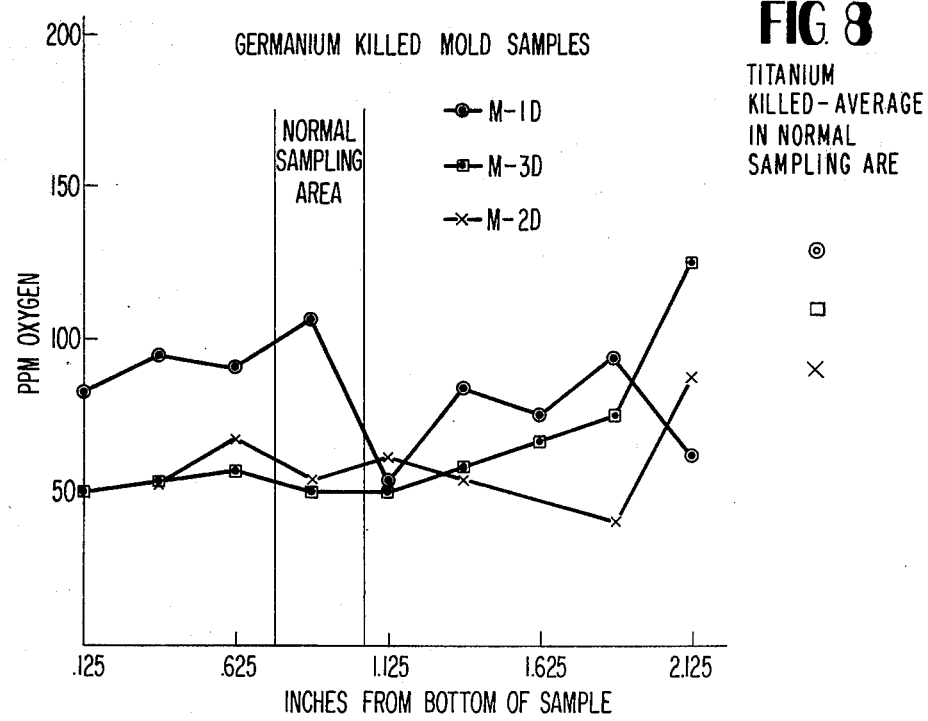

Referring now to FIG. 8, three samples were taken using germanium in the sampling device of FIGS. 4 to 6, the sampling point in this case being at the continuous casting mold after a degassing step. The oxygen content of the steel at this point, as is normal, was much lower and generally is decreasing slightly as the casting progresses. The curves M-1D, M-2D and M-3D show the oxygen content of each sample along the effective length of the sample. Since the samples were taken in the chronological order M-1D, M-2D, M-3D, the oxygen content would be expected to remain the same or decrease slightly and the three curves show this to be true. On the other hand, three titanium killed samples were taken at the same times in the same chronological order and were given the same identification, the average oxygen content of each of these samples in the normal sampling area being shown on the right-hand side of FIG. 8. It will be noted that the titanium killed samples have a higher oxygen content. This verifies the fact that titanium introduces extraneous oxygen into samples, due to the presence of surface oxides on the titanium, whereas metallic germanium does not introduce extraneous oxygen or if it does, the quantity is measurably less than that introduced by titanium. It will also be noted that in the titanium killed samples, the M-3D sample, which should have the least oxygen content, has nearly as much as the M-1D sample and considerably more than the M-2D sample. This indicates that the titanium killed sample M-3D did not give the proper oxygen content for the molten steel in the continuous casting mold.

It is understood that the term "unkilled steel," as used in this patent application is intended to embrace partially killed steel and steel in general which has a dissolved oxygen content that is too high to produce a solidified test ingot suitable for analyzing without adding a killing agent to the molten steel sample prior to solidification.

The foregoing detailed description and the following specific example are for purpose of illustration only.

EXAMPLE

A heat of low carbon steel is prepared by a basic oxygen process following prior art steel making practices and the heat is tapped into a ladle. The steel has a temperature of about 2900° and the oxygen content in the steel as tapped is about 500 parts per million. An elongated bar of aluminum is dissolved in the molten steel in the ladle as the steel enters the ladle from the furnace and the oxygen content of the steel following this aluminum addition is approximately 250 parts per million.

The sampling device illustrated in FIGS. 3 to 6 is inserted into the ladle through the layer of slag on the surface of the molten steel and into the body of the molten steel to obtain a sample. The cavity in the sampling device contains 0.167 percent by weight of metallic germanium in the form of a button. Since the sample weighs approximately 600 grams, the button of germanium weighs one gram. The resulting killed sample is removed from the sampling device and sent to the laboratory where a slice across the longitudinal axis of the sample about a quarter of an inch thick is used as the source of specimens for testing to determine the oxygen content of the steel in the ladle. Of course, other tests are also performed on the sample.

A further advantage of this invention should be noted. It is quite common to find discrepancies in comparing the nitrogen analysis of finished steel with the nitrogen analysis of a sample of that same steel taken at the molten stage and killed with previously known killing agents. These discrepancies arise because in killing the molten steel sample, with titanium for example, the titanium reacts with at least a portion of the available nitrogen to form titanium nitrides which have melting points far in excess of the molten steel, and in fact so high that even at the high temperatures of the analytical procedure, (i.e., around 5000° F) it is unlikely that the nitrides will break down to liberate available nitrogen. Thus, since part of the nitrogen in the sample will be tied up as nitrides, a false reading will be given indicating a nitrogen content in the sample below its true value. This is not the case where germanium is used as in the present invention since any possible reaction product, i.e., germanium dinitride ($Ge_3N_2$), would sublimate at the temperature of the molten metal. Thus, the total amount of nitrogen in the sample is available for analysis.

The above embodiments are to be considered in all respects as illustrative and not restrictive since the invention may be embodied in other specific forms without departing from its spirit or essential characteristics. Therefore, the scope of the invention is indicated by the claims rather than by the foregoing description, and all changes which come within the meaning and range of the equivalents of the claims are intended to be embraced therein.

I claim:
1. A molten metal sampling device for obtaining a test specimen of molten metal so as to determine an oxygen content in the metal comprising
    means forming a mold cavity for the reception of molten metal being sampled and the formation of a solid sample,
    a killing agent for the molten metal in the cavity, the killing agent having as an essential ingredient metallic germanium in quantity sufficient to kill the molten metal in at least part of the cavity so as to form a sound sample for analysis.
2. A molten steel sampling device for obtaining a test specimen of the steel during the manufacture of the steel comprising
    means forming a mold cavity for the reception of molten steel being sampled and the formation of a solid sample,
    a killing agent for the molten steel in the cavity, the killing agent having as an essential element metallic germanium in quantity between about 0.01 and about 1.0% by weight of the sample.
3. A molten steel sampling device for obtaining a test specimen of steel during the manufacture of the steel comprising
    means forming a mold cavity for the reception of molten steel being sampled and the formation of a solid sample,
    a killing agent for the molten steel in the cavity, the killing agent having as an essential ingredient metallic germanium in quantity sufficient to combine with between 20 to 2000 ppm of oxygen in the molten steel.
4. A method of sampling a bath of molten metal to obtain a test specimen comprising
    providing a sampling device having a mold cavity for receiving molten metal to be solidified to form a sample,
    introducing molten metal from the bath into the mold cavity,
    contacting the molten metal in the mold cavity with a killing agent having as an essential ingredient metallic germanium in quantity sufficient to combine with the oxygen in the molten metal forming germanium dioxide to kill the metal in at least a portion of the cavity, and
    solidifying the killed molten metal to form a sample from which a test specimen can be obtained.
5. A method as defined in claim 4 wherein the metal is an alloy having a melting point up to 3200° F.
6. A method as defined in claim 5 wherein the metal is an alloy selected from the group consisting of STELLITE, lead, copper, titanium, tungsten, molybdenum, columbium and thorium based alloys.
7. A method as defined in claim 4 wherein the molten metal is steel.
8. A method of sampling a bath of molten steel to obtain a test specimen comprising
    providing a sampling device having a mold cavity for receiving molten steel to be solidified to form a sample, introducing molten steel from the bath into the mold cavity, contacting the molten steel in the mold cavity with a killing agent having as an essential ingredient metallic germanium in quantity between 0.01 and 0.50% by weight of the sample, the contact between the killing agent and the molten steel in the cavity being such as to obtain thorough mixing of the two in at least a portion of the cavity to form germanium dioxide and thereby kill the molten steel, and solidifying the killed molten steel to form a sample from which a test specimen can be obtained.

9. A method of sampling a bath of molten steel to obtain a test specimen comprising providing a sampling device having a mold cavity for receiving molten steel to be solidified to form a sample, introducing molten steel from the bath into the mold cavity, contacting the molten steel in the mold cavity with a killing agent having as an essential ingredient metallic germanium in quantity sufficient to combine with between 20 and 2000 ppm of oxygen in the molten steel so as to form germanium dioxide, the contact between the killing agent and the molten steel in the cavity being such as to obtain thorough mixing of the two in at least a portion of the cavity, and solidifying the molten steel treated with the killing agent to form a sample from which a test specimen can be obtained.

* * * * *

UNITED STATES PATENT OFFICE
CERTIFICATE OF CORRECTION

Patent No. 4,067,242      Dated Jan. 10, 1978

Inventor(s) James R. Judge

It is certified that error appears in the above-identified patent and that said Letters Patent are hereby corrected as shown below:

Column 2, line 4, after "in" insert -- use --.

Column 2, line 9, after "quantity" delete "of" and insert -- by --.

Column 4, line 55, after "cavity" delete "of" and insert -- in --.

Column 4, line 63, change "16" to -- 116 --.

Column 5, line 9, change "Example" to -- Examples --.

Signed and Sealed this

Thirteenth Day of June 1978

[SEAL]

Attest:

RUTH C. MASON
*Attesting Officer*

DONALD W. BANNER
*Commissioner of Patents and Trademarks*